US006214320B1

(12) United States Patent
Gaffar et al.

(10) Patent No.: US 6,214,320 B1
(45) Date of Patent: *Apr. 10, 2001

(54) ORAL COMPOSITIONS CONTAINING ANTICALCULUS AND ANTIPLAQUE AGENTS

(75) Inventors: Abdul Gaffar, Princeton; John J. Affilitto, Brookside; Thomas G. Polefka, Somerset; Nuran Nabi, North Brunswick; Marilou T. Joziak, South River, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/926,016

(22) Filed: Aug. 7, 1992

Related U.S. Application Data

(63) Continuation-in-part of application No. 07/794,783, filed on Nov. 25, 1991, now Pat. No. 5,208,009, which is a continuation-in-part of application No. 07/631,232, filed on Dec. 20, 1990, now Pat. No. 5,096,699, and a continuation-in-part of application No. 07/594,598, filed on Oct. 9, 1990, now Pat. No. 5,158,763.

(51) Int. Cl.[7] ..................................................... A61K 7/16
(52) U.S. Cl. ................................................................ 424/49
(58) Field of Search ............................................. 424/49–88

(56) References Cited

U.S. PATENT DOCUMENTS

| | | |
|---|---|---|
| 2,863,919 | 12/1958 | Birtwell et al. . |
| 2,984,639 | 5/1961 | Stamberger et al. . |
| 3,328,402 | 6/1967 | Winter . |
| 3,431,208 | 3/1969 | Bailey . |
| 3,468,898 | 9/1969 | Cutler et al. . |
| 3,488,419 * | 1/1970 | McCune et al. ........................ 424/49 |
| 3,671,644 * | 6/1972 | Irani et al. ............................ 424/346 |
| 3,678,154 * | 7/1972 | Widder et al. ......................... 424/52 |
| 3,703,583 | 11/1972 | Martin . |
| 3,737,522 * | 6/1973 | Francis et al. .......................... 424/49 |
| 3,934,002 * | 1/1976 | Haefele ................................. 424/49 |
| 3,937,807 * | 2/1976 | Haefele ................................. 424/52 |
| 3,941,772 * | 3/1976 | Ploger et al. .......................... 260/239 |
| 3,959,458 * | 5/1976 | Agricola et al. ....................... 424/52 |
| 3,988,443 * | 10/1976 | Ploger et al. .......................... 424/200 |
| 4,022,880 * | 5/1977 | Vinson et al. .......................... 424/49 |
| 4,025,616 * | 5/1977 | Haefele ................................. 424/52 |
| 4,042,679 | 8/1977 | Gaffar . |
| 4,118,472 | 10/1978 | Gaffar . |
| 4,118,474 | 10/1978 | Gaffar . |
| 4,224,309 | 9/1980 | Gaffar et al. . |
| 4,569,838 * | 2/1986 | de Vries ................................ 424/49 |
| 4,575,456 | 3/1986 | Hayes . |
| 4,659,504 * | 4/1987 | Hayes ................................ 252/315.3 |
| 4,820,507 * | 4/1989 | Klueppel et al. ....................... 424/54 |
| 4,877,603 * | 10/1989 | Degenhardt et al. .................. 424/57 |
| 5,015,466 * | 5/1991 | Parran et al. .......................... 424/52 |
| 5,015,467 * | 5/1991 | Smitherman ......................... 424/52 |
| 5,032,386 * | 7/1991 | Gaffar et al. .......................... 424/49 |
| 5,096,699 * | 3/1992 | Gaffar et al. .......................... 424/49 |
| 5,158,763 * | 10/1992 | Gaffar et al. .......................... 424/54 |
| 5,208,009 * | 5/1993 | Gaffar et al. .......................... 424/49 |
| 5,240,697 * | 8/1993 | Norfleet et al. ........................ 424/52 |
| 5,578,295 * | 11/1996 | Francis et al. ......................... 424/57 |

FOREIGN PATENT DOCUMENTS

| | | |
|---|---|---|
| 1938177 * | 2/1971 | (DE) . |
| 1938178 * | 2/1971 | (DE) . |
| 23 32 383 | 1/1974 | (DE) . |
| OLS 3532860 | 3/1987 | (DE) . |
| 0161898 | 11/1985 | (EP) . |
| 0161899 | 11/1985 | (EP) . |
| 321233 * | 6/1989 | (EP) . |
| 0220890 | 7/1991 | (EP) . |
| 480811 * | 4/1992 | (EP) . |
| 492998 * | 7/1992 | (EP) . |
| 2055579 * | 4/1971 | (FR) . |
| 2055580 * | 4/1971 | (FR) . |
| 2361865 | 3/1978 | (FR) . |
| 825577 | 12/1959 | (GB) . |
| 1110987 * | 4/1968 | (GB) . |
| 1263934 * | 2/1972 | (GB) . |
| 1319396 | 6/1973 | (GB) . |
| 60/58500 * | 4/1985 | (JP) . |
| 92/00721 * | 1/1992 | (WO) . |
| WO 92/00721 A1 * | 1/1992 | (WO) . |

OTHER PUBLICATIONS

Thera–Med AHP+Fluor Product Label—1986.
A. Gaffar et al, Journal of Dental Research, vol. 60, No. 8, pp. 1432–1439 (Aug. 1981).
"Quaternary Ammonium and Related Compounds in the Article on Antiseptic and Disinfectants," Kirk–Othermer Encyclopedia of Chemical Technology, Second Edition (vol. 2, pp. 632–635).

* cited by examiner

*Primary Examiner*—Shep K. Rose
(74) *Attorney, Agent, or Firm*—Connolly Bove Lodge & Hutz LLP

(57) ABSTRACT

An antiplaque and anticalculus oral composition containing an antimicrobial agent such as chlorohexidine or triclosan and an azacycloalkane-2,2-diphosphonic compound.

9 Claims, No Drawings

ORAL COMPOSITIONS CONTAINING ANTICALCULUS AND ANTIPLAQUE AGENTS

This application is a continuation-in-part of U.S. application Ser. No. 794,783, filed Nov. 25, 1991, now U.S. Pat. No. 5,208,009, which is a continuation-in-part of U.S. application Ser. No. 631,232, filed Dec. 20, 1990, now U.S. Pat. No. 5,096,699, issued Mar. 17, 1992 and of U.S. application Ser. No. 594,598, filed Oct. 9, 1990 now U.S. Pat. No. 5,158,763.

This invention relates to oral compositions containing anticalculus and antiplaque agents. More particularly, it relates to such compositions which are intended for application to the teeth and which have the desirable properties of effectively inhibiting development of dental calculus, which development can lead to gingivitis, as well as inhibiting plaque formation.

Toothpastes and mouthrinses have been manufactured and sold which have had in their formulas components intended to promote dental health, in addition to components intended primarily to clean the teeth and sweeten the breath. For example, fluorides have been successfully included in dentifrice formulations and in mouthrinses for years to harden teeth and reduce caries development, and triclosan and sanguinaria (bloodroot) extract have been employed in dentifrices to reduce plaque formation on the teeth. Azacycloalkane-2,2-diphosphonic acids (AAP's), especially azacyloheptane-2,2-diphosphonic acid (AHP), and salts thereof (also designated AAP and AHP) have been suggested for incorporation in oral composition to reduce tartar (calculus) and plaque because they have the ability to dissolve or prevent deposition on the teeth of difficulty soluble calcium salts as taught in U.S. Pat. Nos. 3,941,772 and 3,988,443 to Ploger et al. In point of fact AAP's are more effective in reducing calculus than in reducing plaque. Accordingly, oral compositions effective against both calculus and plaque have been difficult to achieve.

In accordance with the present invention an anticalculus and antiplaque oral composition comprises an orally acceptable vehicle or carrier for such composition, an effective amount of an orally acceptable azacycloalkane-2,2-diphosphonic compound (AAP) anticalculus agent and an effective amount of certain antimicrobial agents.

It is a further advantage of this invention that when the antiplaque agent is a cationic antimicrobial (i.e. antibacterial) agent staining or discoloration of dental surfaces is reduced.

Other advantages will be apparent from consideration of the following specification.

Applicants are aware of and call attention to the following patent art of interest:

U.S. Pat. Nos. 3,941,772 and 3,988,443, which relate to azacycloalkane-2,2-diphosphonic acids and their uses in toothpastes and mouthwashes.

Patents starting with British Patent 825,577 to Clemow et al which disclose 1,6-di-4'-chlorophenyl-diguanidohexane (chlorhexidine) as a cationic antimicrobial agent effective to inhibit the effect of oral bacteria which cause plaque formation. Chlorhexidine and numerous other cationic antimicrobial agents have, therefore, been recommended to inhibit plaque formation. However, use of cationic antimicrobial agents has led to the staining or discoloration of dental surfaces.

The reason for the formation of such dental stain has not been clearly established. It is believed, however, that stain results from the entrapment of stain chromophores in dental calculus. Cationic antimicrobials enhance the staining process by accelerating both the formation of the stain chromophores and the deposition of calculus. This phenomenon is described in A. Gaffar et al., Journal of Dental Research, Vol. 60, No. 8, pp. 1432–1439 (August 1981).

The art has long sought to employ additives which reduce the dental staining properties of antibacterial agents. Thus, for example, in U.S. Pat. No. 3,934,002 to Haefele the staining properties of bis-biguanide compounds are sought to be inhibited by the inclusion of such compounds as zinc phenol sulfonates hydroxy quinoline, homopolymers and copolymers of aliphatic polycarboxylic acids, certain polyphosphates, certain salts of rare earth metals, phytic acid and certain polyphosphonates and ammonium polyphosphonates. In U.S. Pat. No. 4,042,679 to Gaffar the staining properties of bis-biguanido hexanes and quaternary ammonium salts such as benzethonium chloride and cetyl pyridinium chloride are said to be inhibited by employing as an antistain additive, a polymeric polyphosphonic compound such as polyalkyl bis-(phosphonomethylene) amine acid. In U.S. Pat. No. 4,224,309 to Gaffar et al, the antistaining properties of such bis-biguanido hexanes and quaternary ammonium salts are said to be inhibited by employing as an antistain additive a 2-phosphono-butane-1,2,4-tricarboxylic acid compound. In U.S. Pat. No. 4,118,474 to Gaffar et al, the antistaining properties of such antibacterial agents are said to be inhibited by employing as an antistain additive phosphonoacetic acid and its salts.

For one reason or another, these prior suggestions have not proven to be widely used. For example, previously employed additives which reduced dental staining by cationic antibacterial antiplaque agents also generally reduced their antibacterial and antiplaque activities as by forming a precipitate with such agents.

U.S. Pat. No. 4,022,880 to Vinson et al discloses non-cationic antimicrobial agents such as triclosan (2'4,4'-trichloro-2-hydroxydiphenyl ether, sometimes known as 5-chloro-2-(2,4-dichlorophenoxy) phenol) as antiplaque agents as well cationic antimicrobial agents together with a source of zinc ions, which acts as an anticalculus agent. In German OLS 3532860, triclosan is disclosed in a dentifrice with a copper compound. Other disclosures of triclosan in oral compositions are in EP 0161898, 0161899 and 0220890.

Thus, the present invention of an oral composition with properties to inhibit both calculus and plaque is particularly remarkable. Moreover, when cationic antibacterial agent is employed success against staining is achieved without decreasing the antibacterial, antiplaque activity of the antibacterial agent, a result, which thus far, has eluded the art.

From a review of the art it appears that AAP including AHP and antimicrobial agents including cationic agents such as chlorhexidine and noncationic agents such as triclosan are known dentifrice components separately but no prior art references are known to applicants in which AAP and the antimicrobial agents are present together or in which such preparations are suggested.

The AAP or azacycloalkane-2,2-diphosphonic compound of the invented compositions is an orally acceptable phosphonic acid or salt thereof, which provides a source of an azacycloalkane 2,2-diphosphonate anion. If the salt is employed it will usually be the sodium or potassium salt and will be water soluble. Preparation of AAP is taught in U.S. Pat. No. 3,941,772 to Ploger and its division U.S. Pat. No. 3,988,443, the disclosures of which are incorporated herein by reference. If a salt is to be used it will preferably be one wherein more than one of the phosphonic hydroxyl hydrogens is replaced by the desired alkali metal, such as sodium. The acid form of the AAP is of the following formula:

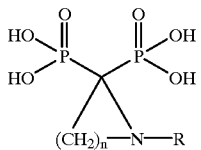

wherein R is selected from the group consisting of hydrogen and alkyls of 1 to 3 carbon atoms and n is an integer from 3 to 5. Preferably R will be hydrogen and n will be 5, forming an azacycloheptyl group (AHP). Although the salts of the described diphosphonic acids may be employed in the present compositions, for example, alkali metal salts, e.g. lithium, sodium or potassium salts and ammonium salts. and although the acid form may be converted or partially converted to salt form in situ in some oral preparations, it will generally be preferred to utilize the acid form of the AAP in the present compositions.

It will be noted that it has been said herein that the AAP utilized should be "orally acceptable". In the present context and throughout this specification that means that the material so specified should be non-toxic, harmless to the mouth, gums and teeth, and of acceptable flavor (or none at all). It should also be essentially compatible with the other components of the oral preparation in which it is to be formulated. It has been determined that the described AAP's satisfactorily pass such tests.

The azacycloalkane diphosphonic acid or salt thereof (AAP) additives should be present in the oral composition of this invention in an effective quantity, typically of from about 0.1 to about 10 times the weight of the antimicrobial agent e.g., from about 0.001 to about 10% by weight of the oral composition. Preferably the AAP is present in a quantity, by weight, of from about 1.0 to about 10 times the weight of the antibacterial agent or from about 0.01 to about 5% by weight most preferably about 0.1 to about 5%, of the oral composition.

The antimicrobial agent employed in accordance with this invention may be any of the well known antiplaque cationic antibacterial agents which are known to have dental surface staining characteristics and which may be classified as the bis-biguanide alkanes and the quaternary ammonium salts antimicrobial antiplaque agents or any of the well known non-cationic antimicrobial agents which are effective in inhibiting plaque and are substantially water-insoluble.

Bis-biguanides are described in German Patent Application No. P2,332,383 published on Jan. 10, 1974 and having the generic formula

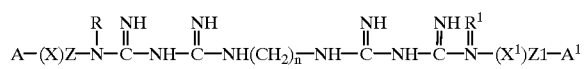

wherein A and Al each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and $X^1$ each represent an alkylene radical containing from 1 to 3 carbon atoms; wherein Z and $Z^1$ each can be either 0 or 1; wherein R and $R^1$ each represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms, aromatic nuclei, etc. Usable water soluble salts of the above are chloride, bromides, sulfates, alkyl sulfonates such as methyl sulfonate and ethyl sulfonate, phenylsulfonates such as p-methylphenyl sulfonates, nitrates, acetates, gluconates, etc.

Examples of suitable bis biquanide compounds are 1,6-bis-(2-ethylhexylbiguanidohexane)dihydrochloride; 1,6-di-($N_1$, $N_1$'-phenyldiguanido-$N_5$, $N_5$')-hexane tetrahydrochloride; 1,6-di-($N_1$, $N_1$,-phenyl-$N_1$, $N_1$'-methyldiguanido-$N_5$, $N_5$') -hexane dihydrochloride; 1,6-di ($N_1$, $N_1$'-o-chlorophenyldiguanido-$N_5$,$N_5$')-hexane dihydrochloride; 1,6-di($N_1$, $N_1$'-2,6-dichlorophenyldiguanido-$N_5$, $N_5$')hexane dihydrochloride; 1,6-di[$N_1$, $N_1$'-β-(p-methoxyphenyl) diguanido-$N_5$, $N_5$']-hexane dihydrochloride; 1,6-di($N_1$, $N_1$'-α-methyl-β-phenyldiguanido-$N_5$, $N_5$')-hexane dihydrochloride; 1,6-di($N_1$, $N_1$'-p-nitrophenyldiguanido-$N_5$, $N_5$')hexane dihydrochloride; ω:ω-di-($N_1$, $N_1$'-phenyldiguanido-$N_5$, $N_5$')-di-n-propylether dihydrochloride; ω:ω-di($N_1$, $N_1$'-p-chlorophenyldiguanido-$N_5$, $N_5$')-di-n-propylether tetrahydrochloride; 1,6-di($N_1$, $N_1$'-2,4-dichlorophenyldiguanido-$N_5$, $N_5$')hexane tetrahydrochloride; 1,6-di($N_1$, $N_1$'-p-methylphenyldiguanido-$N_5$, $N_5$')hexane dihydrochloride; 1,6-di($N_1$, $N_1$'-2,4,5-trichlorophenyldiguanido-$N_5$, $N_5$') hexane tetrahydrochloride; 1,6-di[$N_1$, $N_1$'-α-(p-chlorophenyl) ethyldiguanido-$N_5$, $N_5$'] hexane dihydrochloride; ω:ωdi($N_1$, $N_1$'-p-chlorophenyldiguanido-$N_5$, $N_5$')m-xylene dihydrochloride; 1,12-di($N_1$, $N_1$'-p-chlorophenyldiguanido-$N_5$, $N_5$') dodecane dihydrochloride; 1,10-di($N_1$,$N_1$'-phenyldiguanido-$N_5$, $N_5$')-decane tetrahydrochloride; 1,12-di($N_1$, $N_1$'-phenyldiguanido-$N_5$, $N_5$') dodecane tetrahydrochloride; 1,6-di ($N_1$, $N_1$'-o-chlorophenyldiguanido-$N_5$, $N_5$') hexane dihydrochloride; 1,6-di($N_1$,$N_1$'-p-chlorophenyldiguanido-$N_5$, $N_5$')-hexane tetrahydrochloride; ethylene bis (1-tolyl biguanide); ethylene bis (p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenyl biguanide); trimethylene bis(o-tolyl biguanide); N-butyl trimethylene bis (phenyl biguanide); tetramethylene bis(1-tolyl biguanide); the specific compounds disclosed in U.S. Pat. No. 2,863, 919, Birtwell et. al., (Dec. 9, 1958), said patent being incorporated herein by reference; the specific compounds disclosed in U.S. Pat. No. 3,468,898, Cutler et. al., (Sep. 23, 1969), said patent being incorporated herein by reference; and the corresponding pharmaceutically acceptable salts of all of the above such as the acetates; gluconates; hydrochlorides; hydrobromides; citrates; bisulfites; fluorides; polymaleates; N-coconutalkyl sarcosinates; phosphites; hypophosphites; perfluorooctanoates; silicates; sorbates; salicylates; maleates; tartrates; fumarates; ethylenediaminotetraacetates; iminodiacetates; cinnamates; thiocyanates; arginates; pyromellitates; tetracarboxybutyrates; benzoates; glutarates; monofluorophosphates; and perfluoropropionates.

The bis-biguanide of choice is chlorhexidine digluconate.

Usable also as the cationic antimicrobial antiplaque agent in the oral composition of this invention are the antibacterial quaternary ammonium components such as are described under the section on "Quaternary Ammonium and Related Compounds in the article on Antiseptic and Disinfectants" in Kirk-Othermer Enclyclopedia of Chemica Technology, second edition (Vol. 2, p. 632–635), incorporated herein by reference. Among the most common of these antibacterial, antiplaque quaternary ammonium compounds is benzethonium chloride (Hyamine 1622 or diisobutyl phenoxyethyoxyethyl dimethyl benzyl ammonium chloride). In an oral preparation, this material is highly effective in promoting oral hygiene by reducing dental plaque. Agents of this type are described in U.S. Pat. Nos. 2,984,639; 3,328,402; 3,431,208; 3,703,583 and in British Patent No. 1,319,396.

In general, usable quarternary ammonium compounds include those in which one or two of the substituents on the quaternary nitrogen have a carbon chain length, typically as an alkyl group, of some 8 to 20 carbon atoms e.g., 10 to is carbon atoms while the remaining substituents have a lesser number of carbon atoms, typically as alkyl or benzyl group, such as 1 to 7 carbon atoms e.g., methyl or ethyl group. In addition to the benzethonium chloride agent described above, exemplary quaternary nitrogen compounds are benzalkonium chloride, cetalkonium chloride, cetalkonium bromide, cetylpyridinium, coco-amidopropyldimonium hydroxypropylamino hydrolyzed animal protein, domiphen bromide, lauralkonium bromide, lauralkonium chloride, lauraminopropyl acetamidodimonium chloride, laurylpyridinium chloride and others.

Typical examples of water insoluble noncationic antimicrobial agents which are particularly desirable from considerations of antiplaque effective ess, safety and formulation are:

Halogenate Diphenyl Ethers

2',4,4'-trichloro-2'-hydroxy-diphenyl ether (Triclosan)

2,2'-dihydroxy-5,5'-dibromo-diphenyl ether

Halogenated Salicylanilides

4',5'-dibromosalicylanilide 3,4'5'-trichlorosalcylanilide 3,4,5-tribromosalicylanilide 2,3,3',5- tetrachlorosalicylanilide 3,3,3',5-tetrachlorosalicylanilide 3,5-dibromo-3'-trifluoromethyl salicylanilide 5-n-octanoyl-3'-trifluoromethyl salicylanilide 3,5-dibromo-4'trifluoromethyl salicylanilide 3,5-dibromo-3'-trifluoromethyl salicylanilide (Flurophene)

Benzoic Esters

| | |
|---|---|
| Methyl | - p-Hydroxybenzoic Ester |
| Ethyl | - p-Hydroxybenzoic Ester |
| Propyl | - p-Hydroxybenzoic Ester |
| Butyl | - p-Hydroxybenzoic Ester |

Sesquiterpene Alcohols

Farnesol

Nerolidol

Bisabolol

Santalol

Halogenated Carbanilides 3,4,4'-trichlorocarbanilide 3-trifluoromethyl-4,4'-dichlorocarbanilide 3,3,4'-trichlorocarbanilide Phenolic Compounds (including phenol and its homologs, mono- and poly-alkyl and aromatic halo (e.g.,Cl, Br, I)-phenols, resorcinol and catechol and their derivatives and bisphenolic compounds). Such compounds include inter alia:

| Phenol and its Homologs | |
|---|---|
| Phenol | |
| 2-Methyl | - Phenol |
| 3-Methyl | - Phenol |
| 4-Methyl | - Phenol |
| 4-Ethyl | - Phenol |
| 2.4-Dimethyl | - Phenol |
| 2,5-Dimethyl | - Phenol |
| 3,4-Dimethyl | - Phenol |
| 2,6-Dimethyl | - Phenol |
| 4-n-Propyl | - Phenol |
| 4-n-Butyl | - Phenol |
| 4-n-Amyl | - Phenol |
| 4-tert-Amyl | - Phenol |
| 4-n-Hexyl | - Phenol |
| 4-n-Heptyl | - Phenol |
| 2-Methoxy-(2-Propenyl)-Phenol (Eugenol) | |
| 2-Isopropyl-5-Methyl-Phenol (Thymol) | |
| Mono- and Poly-Alkyl and Aromatic Halophenols | |
| Methyl | - p-Chlorophenol |
| Ethyl | - p-Chlorophenol |
| n-Propyl | - p-Chlorophenol |
| n-Butyl | - p-Chlorophenol |
| n-Amyl | - p-Chlorophenol |
| n-Hexyl | - p-Chlorophenol |
| Cyclohexyl | - p-Chlorophenol |
| n-Heptyl | - p-Chlorophenol |
| n-Octyl | - p-Chlorophenol |
| o-Chlorophenol | |
| Methyl | - o-Chlorophenol |
| Ethyl | - o-Chlorophenol |
| n-Propyl | - o-Chlorophenol |
| n-Butyl | - o-Chlorophenol |
| n-Amyl | - o-Chlorophenol |
| Tert-Amyl | - o-Chlorophenol |
| n-Hexyl | - o-Chlorophenol |
| n-Heptyl | - o-Chlorophenol |
| p-Chlorophenol | |
| o-Benzyl | - p-Chlorophenol |
| o-Benzyl-m-methyl | - p-Chlorophenol |
| o-Benzyl-m-m-dimethyl | - p-Chlorophenol |
| o-Phenylethyl | - p-Chlorophenol |
| o-Phenylethyl-m-methyl | - p-Chlorophenol |
| 3-Methyl | - p-Chlorophenol |
| 3,5-Dimethyl | - p-Chlorophenol |
| 6-Ethyl-3-methyl | - p-Chlorophenol |
| 6-n-Propyl-3-methyl | - p-Chlorophenol |
| 6-iso-Propyl-3-methyl | - p-Chlorophenol |
| 2-Ethyl-3,5-dimethyl | - p-Chlorophenol |
| 6-sec Butyl-3-methyl | - p-Chlorophenol |
| 2-iso-Propyl-3-5-methyl | - p-Chlorophenol |
| 6-Diethylmethyl-3-methyl | - p-Chlorophenol |
| 6-iso-Propyl-2-ethyl-3-methyl | - p-Chlorophenol |
| 2-sec amyl-3,5-dimethyl | - p-Chlorophenol |
| 2-Diethylmethyl-3,5-dimethyl | - p-Chlorophenol |
| 6-sec Octyl-3-methyl | - p-Chlorophenol |
| p-Bromophenol | |
| Methyl | - p-Bromophenol |
| Ethyl | - p-Bromophenol |
| n-Propyl | - p-Bromophenol |

-continued

| | |
|---|---|
| n-Butyl | - p-Bromophenol |
| n-Amyl | - p-Bromophenol |
| sec-Amyl | - p-Bromophenol |
| n-Hexyl | - p-Bromophenol |
| Cyclohexyl | - p-Bromophenol |
| o-Bromophenol | |
| Tert-Amyl | - o-Bromophenol |
| n-Hexyl | - o-Bromophenol |
| n-Propyl-m,m-Dimethyl | - o-Bromophenol |
| 2-Phenyl Phenol | |
| 4-chloro-2-methyl phenol | |
| 4-chloro-3-methyl phenol | |
| 4-chloro-3,5-dimethyl phenol | |
| 2,4-dichloro-3,5-dimethyl phenol | |
| 3,4,5,6-terabromo-2-methylphenol | |
| 5-methyl-2-pentylphenol | |
| 4-isopropyl-3-methylphenol | |
| 5-chloro-2-hydroxydiphenylmethane | |

Resorcinol and Its Derivatives

Resorcinol

| | |
|---|---|
| Methyl | - Resorcinol |
| Ethyl | - Resorcinol |
| n-Propyl | - Resorcinol |
| n-Butyl | - Resorcinol |
| n-Amyl | - Resorcinol |
| n-Hexyl | - Resorcinol |
| n-Heptyl | - Resorcinol |
| n-Octyl | - Resorcinol |
| n-Nonyl | - Resorcinol |
| Phenyl | - Resorcinol |
| Benzyl | - Resorcinol |
| Phenylethyl | - Resorcinol |
| Phenylpropyl | - Resorcinol |
| p-Chlorobenzyl | - Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

Bisphenolic Compounds 2,2'-methylene bis (4-chlorophenol)
2,2'-methylene bis (3,4,6-trichlorophenol)
2,2'-methylene bis (4-chloro-6-bromophenol)
bis (2-hydroxy-3,5-dichlorophenyl) sulfide
bis (2-hydroxy-5-chlorobenzyl) sulfide The oral compositions of the present invention generally contain from about 0.01% to 5% by weight of AAP anticalculus agent, preferably from about 0.2 to about 2%, and still more preferably from about 0.5 to about 1.5%. The amount of antimicrobial or antibacterial antiplaque agent present generally comprises at least 0.01% and may range up to about 5%. When the antimicrobial or antibacterial agent is a bis (halo phenol) compounds such as triclosan, it preferably ranges up to about 1% and when the preferred cyclohexidine or salts thereof are used, the amounts may be up to about 5%.

The preferred noncationic haloo genated diphenyl ether is triclosan. The preferred phenolic compounds are phenol, thymol, eugenol, and 2,2'methylene bis(4-chloro-6-bromophenol).

The antibacterial or antimicrobial anti plaque compound is preferably one which has antibacterial activity such that its phenol co-efficient is well over 50, more preferably well above 100, such as above about 200 or more for S. aureus; for instance, the phenol coefficient (A.O.A.C.) of benzethonium chloride is given by the manufacturer as 410, for S. aureus. when antimicrobial agent is cationic, it will generally be a monomeric (or possibly dimeric) material of molecular weight well below 2,000, such as less than about 1,000. It is, however, within the broader scope of the invention to employ a polymeric cationic antibacterial agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methyl phenyl sulfonate, nitrate, acetate, gluconate, etc.

In the particularly preferred embodiments of this invention the antimicrobial or antibacterial agent is one which contains at least two halo substituted phenyl groups, which may be separated by any suitable divalent moiety such as oxygen, sulfur, alkylene (preferably $C_{1-3}$) or various nitrogen containing groups. Still more preferred are such antimicrobial or antibacterial agents where the halo substituted phenyl groups each has para chloro substituents.

Triclosan is a particularly preferred bisphenolic antimicrobial agent having the formula

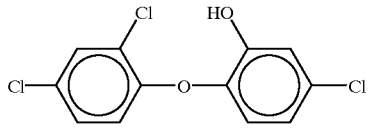

In this instance the two halo phenyl groups (each containing para chloro substituents) are separated by oxygen.

Another particularly preferred antimicrobial agent is chlorhexidine or an appropriate salt thereof. Chlorhexidine is a bis-biguanide which contains two groups of the formula

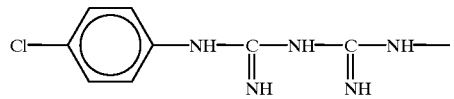

Hereafter, these particularly preferred antimicrobial agents will be called bis(halophenyl) or, in their most preferred form, bis(p-chlorophenyl) antimicrobial or antibacterial agents, it being understood that such agents may have the most preferred general formula

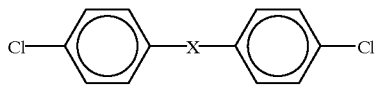

where the phenyl moieties may be additionally substituted with any suitable substituent(s) and X is a divalent radical which is consistent with the antimicrobial properties of the resulting compound.

When these preferred embodiments of antimicrobial or antibacterial agents are employed, the preferred anticalculus agent is one which provides the 1-azacycloheptylidene-2,2-diphosphonate anion, and it may be in the acid form or a suitable salt thereof may be employed as described earlier.

Still further preferred embodiments of this invention include the above preferred antimicrobial (antiplaque) and anticalculus agents combined with a source of an effective amount of fluoride.

When the antimicrobial agent is noncationic, it is particularly desirable to include in the dentifrice a water soluble or water swellable synthetic anionic polymer (SAP), such as a synthetic anionic polycarboxylate (SAPP) which inhibits growth of hydroxyapatite. The SAP has a molecular weight in the range of about 1,000–2,000,000, in a proportion which is effective to increase the anticalculus action of the AAP in the described composition.

U.S. Pat. Nos. 4,323,551, 4,515,772, 4,627,977 and 4,931,273, which disclose SAPP's such as a copolymer of maleic anhydride or maleic acid with vinyl methyl ether (Gantrez) in dentifrices, as do published European Patent Applications Nos. 89114192.1 and 89200710.5 and U.S. patent applications Ser. Nos. 07/505,628, 07/547,641 and 07/547,642 (with the last three U.S. Applications also disclosing triclosan in such dentifrices as an antibacterial agent which inhibits deposition of plaque on the teeth) and SAP's, in addition to the SAPP's.

No references are known to applicants in which AAP, SAP and noncationic antimicrobial agent such as triclosan are present together or in which any AAP and SAP are present together in a dentifrice or other oral preparation, or in which such preparations are suggested. The unexpectedly beneficial improvement in the anticalculus action of the AAP that results from incorporation of the SAP in oral compositions with the AAP is very surprising in view of the negligible anticalculus activity of the SAP alone in such compositions. The improvement is significant, often being more than 30% by both in vitro testing, in which precipitation of hydroxyapatite from a supersaturated solution onto hard substrates was delayed by that much time, and by in vivo testing, in which calculus formation, as actually measured, was found to have been decreased.

Although SAPP's and other SAP's effectively inhibit hydroxyapatite crystal growth they have not been effective in inhibiting calculus formation. Without being bound by a theory, it is believed that this is because of two competing phenomena. First, when hydroxyapatite crystals grow, they grow at their fronts. The anionic polymers are adsorbed onto the growing fronts and their presences appear to inhibit substantial crystal growth at the adsorption sites because a plurality of growth fronts are needed before the SAP can be buried. However, the competing phenomenon also appears to be related to the size of the anionic polymer molecules, in that larger sizes prevent the adsorption of SAP and the filling of all growing crystal front sites of the hydroxyapatite.

The success when SAP is employed appears to result from the unexpected capability of AAP to fill the front sites which are not reached by the SAP, in addition to the effectiveness of AAP itself for inhibition of crystal growth.

When the SAP is an SAPP, it may also function to inhibit the action of alkaline phosphatase enzyme, which otherwise could have a negative effect on polyphosphate, such as pyrophosphate, which can be present as an anticalculus agent in the present compositions, in addition to the AAP. Such SAPP's and their complexes with cationic germicides and metals, such as zinc and magnesium, have been described in U.S. Pat. Nos. 3,429,963, 3,956,480, 4,138,477, 4,152,420, 4,183,914 and 4,627,977.

The hydroxyapatite crystal growth inhibiting polymer is generically a synthetic anionic polymer including, for example, oligomers, homopolymers, copolymers of two or more monomers, ionomers, block copolymers, graft copolymers, cross-linked polymers, cross-linked copolymers, and the like. It is water (saliva) soluble or swellable (hydratable, hydrogel forming). It preferably has an (weight) average molecular weight of about 1,000 to about 2,000,000, preferably about 1,000 to about 1,000,000, more preferably about 2,000, 2,500 or 6,000 to about 100,000, 250,000 or 500,000, a very preferably about 6,000 to about 100,000.

The SAP ordinarily contains at least one acidic group, such as sulfonic, phosphinic or carboxylic, more preferably phosphonic or carboxylic or salt thereof, e.g. alkali metal or ammonium salt, and may also contain at least one organic group, preferably a plurality of both the acidic and organic groups. The organic groups preferably have the formula —(X)n—R wherein X is O, N, S, SO, $SO_2$, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents of R which are generally non-hydrophilic and do not significantly interfere with the desired functions of the SAP of hydroxyapatite crystal growth. The organic groups which may be present are described in British Published Patent Specification 2235133A, which is incorporated herein by reference. SAP's containing such organic groups should remain water soluble or swellable. When the SAP is a cross-linked polymer, a higher molecular weight, more hydrophobic cross-linking moiety can be present in such polymer.

Preferably, the SAP is an anionic polymer comprising a chain or backbone containing repeating units, each preferably containing at least one carbon atom and preferably at least one directly or indirectly pendent, monovalent acidic group. It may also contain at least one directly or indirectly pendent monovalent organic group seminally, vicinally or, less preferably, otherwise bonded to atoms, preferably carbon, in the chain, so long as the SAP is water soluble or swellable. Less preferably, the polymer may contain acidic groups and/or organic groups and/or other divalent atoms or groups as links in the polymer chain instead of or in addition to carbon atoms, or as cross-linking moieties.

It will be understood that any examples or illustrations of SAP's disclosed herein which do not contain both acidic groups and organic groups can, if desired, be chemically modified in known manner to obtain the preferred SAP's containing both such groups and preferably a plurality of each of such groups. It is desirable that the repeating units in the polymer chain or backbone containing acidic delivery enhancing groups constitute at least about 10%, preferably at least about 50%, and more preferably about 80% to 95% or 100% by weight of the polymer.

According to a preferred embodiment of this invention, the SAP comprises a polymer containing repeating units in which one or more phosphonic acid groups are bonded to one or more carbon atoms in the polymer chain. It is characterized as having recurring groups

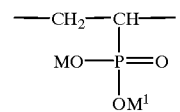

wherein M and $M^1$ are hydrogen, alkali metal or ammonium and are the same or different. A most preferred example of such a SAP is poly- (vinyl phosphonic acid) containing units of the formula:

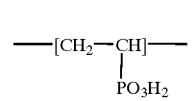

I)

which does not contain the organic group (e.g. —$CH_3$). However, an organic group is present in poly (1-phosphonopropene), with units of the formula:

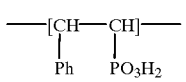
(II)

wherein Ph is phenyl, the phosphonic acidic group and the phenyl organic group being bonded on vicinal carbon atoms in the chain, or a copolymer of beta styrene phosphonic acid with vinyl phosphonyl chloride having the units of formula III alternating or in random association with units of formula I above, or poly (alpha styrene phosphonic acid) containing units of the formula:

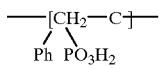
(IV)

in which the acidic and organic groups are geminally bonded to the chain.

The styrene phosphonic acid polymers and their copolymers with other inert ethylenically unsaturated monomers generally have molecular weights in the range of about 2,000 to about 30,000, preferably about 2,500 to about 10,000. Such "inert" monomers do not significantly interfere with the intended function of any copolymer employed as an SAP herein.

As illustrative of SAP's containing phosphinic acidic and/or sulphonic acidic groups, there may be mentioned polymers and copolymers containing units or moieties derived from the polymerization of vinyl or allyl phosphinic and/or sulphonic acids. These may be substituted on the 1- or 2- (or 3-) carbon atom by an organic group, for example, one having the formula $-(X)_n-R$ defined above, so long as the SAP's remain water soluble or swellable. Mixtures of these monomers may be employed, as may be copolymers thereof with one or more inert polymerizable ethylenically unsaturated monomers such as those described above with respect to the operative synthetic anionic polymeric polycarboxylates. As will be noted, in these and other SAP's herein usually only one acidic group is bonded to any given carbon or other atom in the polymer backbone or branch thereon. Polysiloxanes containing or modified to contain pendent acidic groups or organic groups may also be employed as SAP's herein. Also effective as SAP's herein are ionomers containing or modified to contain delivery and retention enhancing groups. Ionomers are described on Pages 546–573 of the Kirk-Othmer Encyclopedia of Chemical Technology, Third Edition, Supplement Volume, John Wiley & Sons, Inc., copyright 1984, which description is incorporated herein by reference.

The described SAPP's are preferably employed as partially or completely neutralized water soluble or water swellable alkali metal (or ammonium) salts but may also be used as their free acids. Preferably they are 4:1 to 1:4 copolymers of maleic anhydride or maleic acid with another, which is very preferably methyl vinyl ether, and the copolymer will have a molecular weight in the range of about 5,000–2,000,000, preferably about 30,000–1,500,000, more preferably about 50,000–1,100,000 and most preferably about 50,000–100,000, as determined by vapor pressure osmometry. A preferred range of molecular weights, by gel permeation chromatography against a polyethylene glycol standard, is about 500,00–1,500,000, more preferably about 1,000,000–1,100,000, e.g. about 1,090,000. Useful such SAPP's include GA's Gantrezes AN 169, AN 139, AN 119 and S-97, pharmaceutical grade. These SAPP's have been reported by their manufacturer to be of molecular weights of about 750,000, 500,000, 250,000 and 70,000, respectively, but by gel permeation chromatography determinations (against a polyethylene glycol standard) the S-97, pharmaceutical grade, is of a molecular weight in the range of about 1,000,000–1,100,000 (the lower molecular weight of 70,000 was determined by vapor pressure osmometry). The mentioned Gantrezes are all linear copolymers, but cross-linked polymers, such as those sold under the trademark Carbopol (Registered Trademark), of B. F. Goodrich, e.g. Carbopols 934, 940 and 941, may be substituted, at least in part e.g. about 1% or more).

Instead of a single SAP, the mentioned mixtures may be employed, for instance, with polymeric polycarboxylates, other SAPP's or other SAP's, such as polysulphonates, polysulphates and polyphosphonates, typically, but not necessarily, with the amount thereof in a proportion not more than about half the SAPP content. The various polymers of such types may be made by reacting an ethylenically unsaturated organic acid, such as maleic, crotonic, sorbic, alphachlorosorbic, cinnamic, muconic, itaconic, citraconic, mesaconic, glutaconic, aconitic, angelic, umbellic, or fumaric, acid(s) or anhydride(s), with an appropriate polymerized ethylenically unsaturated carboxylic, sulphonic, sulphuric or phosphonic acid that contains an activated carbon-to-carbon olefinic double bond and at least one carboxylic, sulphonic, sulphuric or phosphonic group. Other olefinic monomers that are copolymerizable with the described acids or anhydrides include vinyl acetate, vinyl chloride, dimethyl maleate, and similar unsaturated monomers, and the copolymers made will contain a sufficient proportion of acidic groups or neutralized or neutralizable acidic groups to make them water soluble or swellable. Some such polycarboxylate copolymers are those disclosed in U.S. Pat. Nos. 4,138,477 and 4,183,914, and include copolymers of maleic anhydride with styrene, isobutylene or vinyl ethyl ether, polyacrylic, polyitaconic and polymaleic acids, and sulphoacrylic oligomers of comparatively low molecular weights, such as Uniroyal (Registered Trademark) ND-2.

Although Gantrez is the preferred SAPP, also useful in the present compositions as SAPP's or as substitutes for them in part are carboxyvinyl polymers, such as those described in U.S. Pat. Nos. 3,711,604, 3,911,904, 3,919,409, 3,935,306 and 3,980,767, wherein they were employed as components of toothpastes. Such materials are the Carbopols, mentioned previously, which are polymers of polyacrylic acid cross-linked with minor proportions of polyallyl sucrose or polyallyl pentaerythritol, as cross-linking agents. Instead of such polymers there may be employed polycarbophil, such as polyacrylic acid cross-linked with divinyl glycol.

In summary, with respect to the SAPP's, polymers that are most effective will normally be those with a sufficient proportion of carboxyls or neutralized carboxyls to be water soluble or swellable in the present total compositions, and such will also increase the anticalculus effectiveness of AAP.

SAP's that may also be used in oral compositions like those described herein and can increase the anticalculus activity of the AAP are described in British Published Patent Specification 2235133A, in the description therein of antibacterial enhancing agents (AEA's). Such specification was previously incorporated herein by reference and the disclosures of the various other patents, applications and publications referred to in this specification are hereby also so incorporated herein.

In certain highly preferred forms of the invention, the oral composition may be substantially liquid in character, such as a mouthwash or rinse. In such a preparation, the vehicle is typically a water-alcohol mixture. Generally, the ratio of water to alcohol is in the range of from about 1:1 to about 20:1 preferably from 3:1 to 20:1 and most preferably about 17:3, by weight. The total amount of water alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zironium silicates, bentonite, and mixtures thereof. Preferred polishing materials include complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37%, at 100° C., and which has a specific gravity of 2.42 and a particle size such that 100% of the particles are less than 50 microns and 84% of the particles are less than 20 microns, is particularly desirable.

When visually clear gels are employed, polishing agents comprising alkali metal aluminosilicate complexes are particularly useful, since they have refractive indices close to the refractive indices of gelling agent-liquid (including water and/or humectant) systems commonly used in dentifrices.

Many of the so-called "water-soluble" polishing materials are anionic in character and also include small amounts of soluble material., Thus, insoluble sodium metaphosphate may be formed in any suitable manner, as illustrated in Thorpe's Dictionary of Applied Chemistry, Volume 9, Fourth Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 20 to about 99% by weight of the oral preparation. Preferably, it is present in amounts ranging from about 20 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antibacterial antiplaque agent and additive should be compatible with the other components of the preparation. Thus, in a toothpaste, the liquid vehicle may comprise water and humectant typically in an amount ranging from about 10 to about 90% by weight of the preparation. Glycerine, sorbitol, xylitol or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3–30% by weight of water, 0 to about 80% bt weight of glycerine, and about 20–80% by weight of sorbitol is preferably employed. A gelling agent, such as natural or synthetic gums or gumlike materials, typically Irish moss, sodium carboxymethylcelluliose, methyl cellulose, hydroxyethyl cellulose, gum tragacanth, polyvinylpyrrolidone, starch, or preferably hydroxypropyl methyl cellulose or the Carbopols (e.g. 934, 940 and 941) or the like is usually present in toothpaste in an amount up to about 10% by weight, preferably in the range of from about 0.5 to about 5%. In a toothpaste or gel, the liquids and solids are proportioned to form a crymy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-provide compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having alabel describing it, in substance, as a toothpaste or dental cream.

In oral compositions such as mouthrinses and toothpastes, a surfactant is often present, e.g. to promote foaming. It will be understood that it is preferable to employ nonionic or amphotenic surfactants rather than their anionic counterparts. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of ethylene oxide with fatty acids, fatty alcohols and fatty amides including alcohols such as sorbitan monostearate or polypropyleneoxide (that is, Pluronic materials).

Another important active component of preferred embodiments of the invented compositions is a source of fluoride ions, which gives the compositions tooth hardening properties and helps to reduce caries development. The source of fluoride ions is usually inorganic and a salt, and may be fully or slightly soluble in water. Such source is characterized by an ability to release fluoride ions in water and by relative inertness toward other components of the oral compositions. Among the useful sources of fluoride ions are soluble alkali metal fluorides, such as sodium and potassium fluorides, copper fluorides, such as cuprous fluoride, ammonium fluorosilicate, sodium fluorozirconate, ammonium fluorozirconate, sodium monofluorophosphate, alumonium fluorophosphates (mono-, di- and tri-), and fluorinated sodium calcium pyrophosphate. Alkali metal and tin fluorides, such as sodium and stannous fluorides, and sodium monofluorophosphate (MFP (Registered Trademark)) and mixtures thereof are preferred.

The amount of the fluorine-providing compound is dependent to some extent upon the type of compound, its solubility, and the type of oral preparation, but it must be nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, say about 0.01 to 0.15% and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

Another important component is the orally acceptable (that is, toxicologically safe), oral vehicle or carrier which is used in the present compositions, except sometimes for tooth powders, gums and lozenges. In toothpastes and other such paste or gel compositions an aqueous base will be present and in mouthwashes and such types of liquid compositions an aqueous medium will be present, which will usually include an alcohol. The water employed may be city water and the hardness thereof may be as high as 300 or even 500 p.p.m., as calcium carbonate, in some instances, but it will be preferred to limit the hardness to no more than 100 or 150 p.p.m., and it will be more preferred to employ zero hardness water or deionized water, which is most preferably irradiated before being compounded with the other components of the oral compositions. It is highly preferred, if not essential, to add water after the other ingredients (except perhaps for some of the water) are mixed or contacted with each other to avoid a tendency for components to be precipitated.

For the liquid state compositions of this invention, such as mouthrinses or mouthwashes, professionally applied tooth hardeners, and antiplaque compositions, the liquid medium in which the active anticalculus components are dispersed and/or dissolved will normally be aqueous and often will be aqueous alcoholic, with ethanol being the preferred alcohol. A surfactant, such as a detergent, is also preferably present in most such compositions. Other adjuvants may be present too, and sometimes impurities or by-products present with the components, as commercially supplied, will also be present in the final compositions.

For instance, a mouthrinse or mouthwash may be prepared by mixing ethanol and water with flavoring oil, nonionic surfactant, humectant, antimicrobial antiplaque agent, such as benzethonium chloride chlorohexidine or triclosan, sweetener, color and then the above defined antistain additive, followed by additional water as desired.

For the paste, gel, solid and particulate solid state compositions of the invention, such as toothpastes, gel dentifrices, tooth powders, chewing gums and lozenges, the base or medium for the active components will be such as is normally employed for such compositions that don't contain AAP and SAP. For the toothpastes and gel dentifrices such bases will comprise: water, humectant, such as glycerol, sorbitol, mannitol, propylene glycol and/or polyethylene glycol; polishing agent, such as silica, calcium carbonate, tricalcium phosphate, dicalcium phosphate and/or insoluble sodium metaphosphate (of which finely divided silica polishing agent is preferred); and a surfactant, such as sodium lauryl sulphate, sodium N-coco, N-methyl taurate, sodium N-lauroyl sarconsinate or other capatible detergent. The surfactant assists in dissolving substantially water-insoluble noncationic antimicrobial agent, such as triclosan, when present. A thickener, which will preferably be a natural or synthetic gum, such as carrageenan or hydroxymethyl cellulose, or a siliceous thickener (such as fumed silica) or a mixture of such thickeners will often be employed to help to increase paste or gel viscosity or body and in the case of the gel dentifrice it can function as the gelling agent. Other known thickeners and gelling agents may be employed in place of those specifically mentioned above and other known polishing agents, humectants and surfactants may also be used. The bases for the tooth powders will normally be almost entirely of polishing agent, with some surfactant. The base for the gum can be an elastomer of a type normally employed in chewing gums, e.g. chicle, gum or rubber, and the lozenges may have a hard sugar or candy base but preferably will be sorbitol or a gummy material, such as gelatin, sweetened with artificial sweetener, such as saccharin or aspartame.

A toothpaste may be prepared by forming a gel with humectant, gum or thickener such as hydroxyethyl cellulose, sweetener and adding thereto polishing agent, flavor, antibacterial agent, such as benzethonium chloride or chlohexidine, additional water, and then the above-defined antistain additive. If sodium carboxymrthyl cellulose is employed as the gelling agent, the procedure of either U.S. Pat. No. 3,842,168 or U.S. Pat. No. 3,843,779, modified by the inclusion of the additive, is followed.

The various oral compositions of this invention will often contain adjuvants to make them more acceptable to the consumer and more effective for their purposes. Because the compositions are intended for oral uses they will almost invariably include flavouring agents and sweeteners, of which mint flavours, such as peppermint and spearmint, are typical, and saccharin and aspartame are favoured artifical or synethetic sweeteners. Also, adjuvant materials may be present to give the compositions additional desirable properties and to increase desirable characteristics of the compositions. For example, sodium pyrophosphate may be incorporated in the compositions to decrease plaque and tartar, buffers may be added to control pH, bleaching agents and tooth whiteners may be present, and preservatives, dyes and pigments may be employed.

The proportions of the active components of the invented compositions should be within certain ranges to obtain the effects desired. For instance, in oral compositions containing substantially water-insoluble noncationic antimicrobial agent such as triclosan, when SAP is present the proportion of SAP to AAP should be such that the SAP significantly improves the anticalculus effect of the AAP. Such significant effect may be measured in vivo, in which case the improvement obtained shuld be at least 10% more reduction in calculus on human or primate teeth than for a "control" from which the SAP was omited (but in which the AAP was predsent. Thus, for example, if a placebo composition, not containing either AAP or SAP, gives 8.7 units of calculus in primates, using techniques described in *Colloids and Surfaces,* 26 (1987) 109–121, by Gaffar et al, and employing AHP in the same toothpaste lowers calculus formation to 5.7 units, then the experimental composition, containing Gantrez S-97 polycarboxylate as the SAP, and AHP should reduce calculus formed to 5.4 units, or less. Preferably such lowering will be at least 20% and more prefereably will be at least 30%. In actuality, the calculus is reduced to 3.7 units, a reduction of 67%. Instead of employing the mentioned in vivo testm, an in vitro test may be substituted, in which the time of deposition of hydroxyapatite from a supersaturated calcium phosphate solution onto a substrate is measured, using a control (water solution of calcium phosphate), a comparative (water solution of calcium phosphate plus AAP), and a test solution (water solution of calcium phosphate plus AAP and SAP). By such a test it is desirable for the test solution to delay formation of hydroxyapatite for at least ten minutes more than the comparative solution. This in vitro test is described in detail in the text *Recent Advances in the Study of Dental Calculus* (IRL Press) at pages 155–173. The suitability of the in vitro test has been established by parallel testing in vivo, so either test may be employed to determine the effectiveness of different anti-calculus compositions in retarding the deposition of calculus on teeth. The mentioned article and text are both incorporated herein by reference.

Because calculus formation is related to tartar deposition on the teeth and because calculus and tartar are precursors of gum irritation and gingivitis, oral compositions that are effective in inhibiting calculus development on the teeth can help to prevent gingivitis and thereby can help to prevent resulting tooth losses. Therefore, the present compositions are of significant importance in improving dental health, in addition to being of real importance cosmetically by keeping tooth surfaces smooth, clean and bright, and free of calculus and tartar.

When SAP is present, the proportions of AAP and SAP in the compositions will normally be in the range of about 1:50–50:1, with about 1:30–5:1 being preferred and with about 1:10–3:1 being more preferred, e.g. 1:8, 1:5, 1:1 and 2:1. Usually one will not employ more than 3 or 5% of each of AAP and SAP in the compositions and at least about 0.01% of AAP and at least about 0.1% of SAP will be present to obtain the desired effects. In toothpastes, gels and powder products the ranges of contents of AAP and SAP will usually be about 0.2–2% of AAP and about 0.2–3% of SAP, preferably being about 0.5–1.5% and about 0.3–1%, respectively, and more preferably being 0.8–1.2% and 0.3–0.7%, respectively, For the anti-calculus mouthwashes and mouthrinses the ranges of contents of AAP and SAP will usually be about 0.01–2% of AAP and about 0.01–3% of SAP, preferably about 0.1–2% and 0.1–3%, respectively, more preferably about 0.3–1.5% and about 0.1 to 1%, respectively, and most preferably about 0.3–0.7% and about 0.2–0.5%, respectively.

When the noncationic antimicrobial material triclosan is present in the described compositions, for its antiplaque activity, the proportions thereof will normally be within the range of about 0.01–1%, preferably about 0.3–0.6%, with about 0.3–1% and 0.01–0.06% being present in tooth and mouth preparations, respectively. When a source of fluoride ions is present, for its tooth hardening and anticaries actions, the proportion thereof in the oral compositions will normally be in the range of about 0.01–0.5%, based on the fluoride ion content thereof, which corresponds to about 0.02–1% of sodium fluoride. Preferably the percentage of fluoride ion source (as fluoride ion) will be about 0.02–0.3%, which corresponds to about 0.04–0.6% of sodium fluoride, and more preferably such percentage range will be about 0.1–0.2% of such source, which corresponds to about 0.2–0.4% of sodium fluoride.

The proportions and percentages of other components of the oral compositions are not as directly related to the anticalculus, antitartar and antiplaque activities of the oral compositions as those of the AAP, SAP, antimicrobial agent (e.g. triclosan) and fluoride source, as given above, but often will be those which are employed in making conventional oral compositions of the same or similar types. However, they are given here so that the reader will have guidance for making the complete anticalculus compositions.

The toothpastes and gel dentifrices of the invention will preferably contain about 15–45% of humectant and more preferably about 20–35% thereof and such humectant preferably will be selected from the group consisting of glycerol, sorbitol, mannitol, propylene glycol and polyethylene glycols. The polishing agent content will preferably be in the range of about 10–40% and more preferably will be in the range of about 10–25%, with the preferred such agent being a finely divided silica dental polishing agent. Such toothpastes and gel dentifrices will also preferably contain about 0.2–3% of a surfactant (surface active agent) and more preferably the percentage of surfactant will be in the range of about 0.5–2%, and the surfactant will preferably be an acceptable dental detergent, such as sodium lauryl sulphate, other anionic detergent, such as sodium N-lauroyl sarcosine and/or sodium N-lauroyl, N-methyl taurate, amphoteric detergent, such as one that is betaine based, or a nonionic detergent, such as a condensation product of a higher alcohol of 8 to 20 carbon atoms with 1 or 3 to 16 or 20 moles of ethylene oxide, or a nonionic detergent of the Pluronic (Registered Trade Mark) type, e.g. Pluronic L-44. The percentage of thickener is preferably in the range of about 0.5–8%, more preferably about 1–5%, and the thickener is preferably a mixture of organic gum, such as carrageenan, and finely divided silica, such as fumed silica, with the silica thickener often being present in greater proportion.

Various adjuvants present will normally total no more than about 10% of the compositions and often that total will be about 0.1–5%. Such can normally include flavour, colourant, antioxidant, preservative, decorative components, such as speckles, pearlescing agents, bactericides, buffers, anti-enzymatic additives and physiologically active coolants, such as menthol. The balances of the dentifrices will be water and the proportion thereof will ordinarily be in the range of about 20–70%, preferably being in the range of about 35–55%, e.g. 45%.

The toothpastes and gel dentifrices may be packaged in conventional metal or plastic "squeeze tubes", in piston actuated dispensers, in pressurized "aerosol" dispensers or in other suitable containers, which are preferably of the dispensing type. If the container is plastic and the dentifrice contains triclosan it will be preferable to include limonene or other such stabilizing terpene in the flavour or as an adjuvant to stabilize the triclosan against any possible decomposition due to contact with such plastic under elevated temperature storage conditions. Triclosan is not decomposed by all plastics but it may often be advisable to include the stabilizer in the dentifrice formulas as a safety measure.

The mouthrinses or mouthwashes of the invention do not require any additional components than the AAP, antimicrobial agents, alcohol and water, and sometimes the alcohol may be omitted. However, if alcohol is present the proportion thereof will normally be in the range of about 3–30%, preferably about 5–20%, and the balance of the composition will be water and adjuvants, in addition to the AAP and antimicrobial agents. The mouthrinses or mouthwashes may also include the other active components previously mentioned as components of the toothpastes and gel dentifrices, and usually they may be present in the same or lesser percentages, except that normally no polishing agents will be used and the proportion of humectant present, if any, will be reduced, as may be the proportion of surfactant, and water will constitute the balance of the composition, allowing for the presence of a small proportion of adjuvants, such as colourants and flavours. When the mouthrinse contains about 0.1–2% of AAP, about 0.03–0.1% of triclosan, 2% of SAP and about 2–30% of ethanol, for example, the water content 0.5–1.5% of AAP, about 0.3–1% of SAP and about 5–20% of ethanol the water content may be in the range of about 77.5–94.2%

For the tooth powders, the proportions of AAP, antimicrobial agents and surfactant may be the same as for the toothpastes and the balances of such compositions will normally be polishing agent plus the normal content of adjuvant (s), as for the toothpastes. Other tooth treating components may be present too, including pyrophosphate for tartar control.

The tooth hardening liquid compositions, which may be professionally "painted" onto the teeth, and the antiplaque liquid compositions, which may be similarly applied or may be "rinsed" onto the teeth, are similar in composition to the mouthrinses but will also contain a source of fluoride (often in the same or greater proportion as for the toothpaste and fluoride-containing mouthrinse) and antimicrobial agent such as triclosan (also in proportions like those for the mouthwashes and toothpastes), respectively. The gums and lozenges will also contain the same proportions of AAP and antimicrobial agent as the toothpastes, with or without SAP (if the antimicrobial agent is noncationic) fluoride source, surfactant, triclosan and adjuvants, often in the same proportions as for the toothpastes. Water contents and any contents of humectant materials will be adjusted as indicated to be desirable to obtain these products in chewable gum or slowly dissolvable lozenge form.

Manufacturing of dentifrices of this invention is comparatively simple because, in general, there is little or no criticality in the order of addition of the various components present in such compositions. Initially one forms a premix of most or all of the water, in which the surfactant has been dissolved, and then antimicrobial agent is admixed with that, followed by other water soluble components and the water insoluble components, if any. If desired, the lipophilic components may be premixed together and such premix can be mixed with the hydrophiles premix, after which the water insoluble particulate materials may be blended in, as in the cases of toothpastes and gels. Such procedures are typical of those employed in manufacturing toothpastes and dentifrice gels, with the only exception being in the addition of the triclosan, if present, to the water solution of surfactant, as an initial production step.

Manufacture of the mouthrinses or mouthwashes is even simpler because in such cases the ethanol and water are mixed and the various soluble components are then admixed with such aqueous alcoholic medium, with the surfactant and triclosan, if present, preferably being admixed first with the medium. The tooth powder may be made by merely blending the various powdered components thereof and the professional tooth hardening preparations and the antiplaque compositions may be made by following the procedure described for the mouthrinses. Making the gums and lozenges may be by procedures normally employed in manufacturing such products, with the active components usually preferably being added near the end of the manufacturing process if heat is employed (so as to minimize subjection to elevated temperatures).

All the processes for manufacturing the described compositions may be carried out at room temperature, as a rule, except possibly those for making gum and lozenges including AAP and antimicrobial agent, and in such cases heating may be minimized to the extent that such is practicable.

Using the invented compositions is easy, and processes for inhibiting formation of calculus on the teeth normally merely involve employing the preparations containing the AAP and antimicrobial agent in normal manners. Thus, the teeth are brushed with the toothpaste or dentifrice gel, the mouth is rinsed with the mouthrinse or mouthwash, the tooth hardener and antiplaque compositions are applied to the teeth with swabs or by rinsing the mouth with them, the gum is chewed and the lozenge is allowed to dissolve slowly in the saliva in the mouth. In all such cases use of the invented compositions (or of their separate active components) will cause a decrease in calculus development on the teeth. The teeth will be cleaner, whiter, brighter and of better appearance, and development of tartar will be reduced, thereby helping to make the teeth and gums healthier and to prevent gingivitis. If oxidizing agents are present, such as peroxides, the teeth will be still whiter due to bleaching of any food and other stains on them.

The improvements in the teeth, as mentioned above, are noticeable visually and diagnostically after repeated treatments of the teeth with one or more of the invented compositions and for best effects the compositions should be employed at a pH of about 4.5 to about 9, generally about 5.5 to about 8, preferably about 6 to 8, 5 to 7 times a week on a regular daily basis, at least once a day and preferably twice to three times daily for a period of at least a month, and preferably longer. Ideally, such treatments should be ongoing, for months and even for years, just as conventional toothbrushings and uses of mouthrinses are daily or twice daily functions for those who conscientiously care for their teeth. In fact, it is only from such continued regular use that the desirable tooth hardening effects of the fluoride containing products will usually be obtained (unless special professional application of the tooth hardening compositions is made).

The following examples illustrate the invention but do not limit it. Unless otherwise mentioned all parts and percentages in this specification, these examples and the appended claims are by weight and all temperatures are in OC. Also, when molecular weights of the SAPP Gantrez S-97 are are determined by the vapour pressure osmometry method, as employed by the manufacturer, unless the gel permeation chromatography method (against a polyethylene glycol standard is specified.

EXAMPLE 1

Two different mouthrinse formulations containing chlorhexidine gluconate and sodium azacycloheptane diphosphonate (AHP) were prepared for stability and pre-clinical evaluation. The mouthrinse formulae are listed in Table 1. To prepare the mouthrinses, the appropriate quantity of surfactant (PEG-40 sorbitan diisostearate or coco-amidopropyl betaine) and chlorhexidine gluconate were admixed in one-half (½) the rinse's volume of distilled water. With mixing, solution of AHP was added slowly to the chlorhexidine/surfactant solution to yield a final rinse concentration of 0.59% sodium AHP (w/v). The pH of the mouthrinse was adjusted to a value of 7.0 with glacial acetic acid and the remaining ingredients were added at the concentrations shown in Table 1.

TABLE 1

| Ingredients | SAMPLE 1 Betaine Option (%) | SAMPLE 2 Nonionic Option (%) |
|---|---|---|
| Chlorhexidine gluconate (A.I.) | 0.12 | 0.12 |
| Coco-amidopropyl betaine (A.I) | 0.25 | — |
| PEG Sorbitan diisostearate | — | 0.12 |
| Sod. AHP | 0.59 | 0.59 |
| Sod. saccharin | 0.01 | 0.01 |
| Glycerine | 10.00 | 10.00 |
| Ethanol | 10.00 | 10.00 |
| Flavor | 0.04 | 0.04 |
| Water | Q.S. to 100.00 | Q.S. to 100.00 |
| pH | 7.00 | 7.00 |

EXAMPLE 2

Nine week accelerated aging tests were conducted for the mouthrinses described in Example 1. The concentration of chlorhexidine (CHX) was measured by the method of Gaffney and Cooke (J. Chromato. (1984) 306:303–313) whereas AHP was determined via Dionex chromatography. Table 2 illustrates the data obtained.

TABLE 2

| Mouthrinse | Temp (° C.) | Percent Recovery of Actives (%) CHX | AHP | Physical Appearance |
|---|---|---|---|---|
| CHX Solution | 25 | 102 | — | Clear Sol. |
| Control | 49 | 105 | — | Clear Sol. |
| AHP Solution | 25 | — | 102 | Clear Sol. |
| Control | 49 | — | 107 | Clear Sol. |
| Sample 1 | | | | |
| (CHX/Betaine/AHP mouthrinse) | 25 | 101 | 100 | Clear Sol. |
| | 49 | 100 | 105 | Clear Sol. |
| Sample 2 | | | | |
| (CHX/Nonionic/AHP mouthrinse) | 25 | 108 | 92 | Clear Sol. |
| | 49 | 96 | 91 | Clear Sol. |

The CHX solution control was a 0.12% CHX, by weight, aqueous solution. The AHP solution control was a 0.6% AHP, by weight, aqueous solution. After 9 weeks aging at 25° C. both mouthrinse formulations, Samples 1 and 2 were optically clear and devoid of precipitation. The stability of the rinses stored at 49° C. were acceptable, although the nonionic option exhibited a trace of precipitation. To overcome this it is preferred that the concentration of PEG-40 sorbitan diisostearate be increased to 0.225%.

EXAMPLE 3

The antiplaque activity of a chlorhexidine solution or mouthrinse was measured by an in vitro plaque assay. Extracted, noncarious human incisors were cleaned of gross deposits and polished with pumice using a dental drill. The root surface was removed at the cemento-enamel junction and the enamel portion of the tooth was attached to nichrome wire with the aid of epoxy. Each tooth was suspended from a cap (10 dram vial) such that the tooth would be submerged when the vial contained 10 ml of liquid. The teeth were sterilized by irradiation with UV light for 2 hours. After sterilization, the teeth wee treated for 30 seconds with the appropriate mouthrinse, washed extensively with Resting Saliva Salts Buffer (1.1 mM $CaCl_2$, 0.6 mM $KH_2PO_4$, 50 mM NaCl—pH 7.0), and aseptically transferred to vials containing 10 ml Trypticase Soy broth (Difco) with 3% sucrose which had been pre-inoculated to a high cell density with an 18 hours culture of *Actinomyces viscous* T14v and *Streptococcus mutans* JBP. After 24 hours of plaque development, the teeth were retreated with the test mouthrinses and then transferred to new vials pre-inoculated with bacteria. The treatment and plaque growth procedure was repeated for four successive days at which time plaque was removed from the teeth by exposing the teeth to sonic energy. Plaque was quantified by measuring the bacterial deoxyribonucleic acid (DNA) associated with each tooth according to the fluorescence DNA assay of Labarca and Paigen (Anal. Biochem. (1980) 102:344–352). Table 3 summarizes the data obtained.

TABLE 3

| Rinse | N* | Plaque DNA Recovered (ug/tooth Percent ± SD) | Reduction (%) |
|---|---|---|---|
| Control (water) | 5 | 96 ± 13 | — |
| Commercial CHX Product | 5 | 35 ± 19 | 63 |
| CHX/Nonionic/AHP-Sample 2 | 5 | 17 ± 9 | 82 |
| CHX/0.25% Bet/AHP-Sample 1 | 5 | 13 ± 12 | 86 |

*Number of Samples

The data in Table 3 shows clearly that both chlorhexidine/AHP mouthrinses significantly (P<0.05) reduced the formation of in vitro plaque. Indeed, the mouthrinses containing AHP appear to exhibit greater antiplaque efficacy than a commercially available chlorhexidine product.

EXAMPLE 4

An in vitro assay was used to assess the staining potential of the chlorhexidine mouthrinses. Into a two ounce bottle was added the following: 1.0 gram hydroxyapatite beads, 1.25 ml 0.1 sodium phosphate buffer (pH 7.0), 5 ml 0.1 M sodium phosphate buffer (pH 7.0) containing 2.5% Bovine Serum Albumine (Sigma Chemical Co., Type V), 12.5 ml test mouthrinse, and 6 ml 30% acetaldehyde prepared in 0.1 M sodium phosphate buffer (pH 7.0). The mixture was shaken vigorously for 72 hours at 37° C. After this incubation, the solid was collected by filtration, washed with 10 ml 0.1 M sodium phosphate buffer (pH 7.0), and dried for 24 hours at 37° C. The color retained to the hydroxyapatite was measured using a Gardner Reflectometer (Pacific Scientific, Silver Springs, Md.) and is expressed as reflectance (RD) units (i.e. the lower the reflectance, the greater the stain). Table 4 summarizes the data obtained.

TABLE 4

| Mouthrinse | N* | Mean Stain (RD ± SD) | Relative Stain |
|---|---|---|---|
| Water Control | 4 | 52 ± 1 | 0 |
| Chlorhexidine Soln | 4 | 34 ± 1 | 100 |
| CHX/betaine/AHP | 4 | 43 ± 1 | 52 |
| CHX/nonionic/AHP | 4 | 46 ± 1 | 32 |

*Number of Samples

The data of Table 4 clearly illustrates the antistaining characteristics of the chlorhexine/AHP compositions.

EXAMPLE 5

An oral composition of this invention is prepared as a dentifrice having the formula shown in Table 5.

TABLE 5

| Ingredient | Percent (%) |
|---|---|
| Chlorhexidine Gluconate (A.I.) | 0.89 |
| Coco-amidopropyl Betaine (A.I.) | 1.50 |
| Xylitol | 20.00 |
| Sodium Azacycloheptane Diphosphate | 1.00 |
| Sodium Saccharin | 0.06 |
| Sodium Fluoride | 0.24 |
| Diatomaceous Earth Abrasive | 20.00 |
| Hydroxyethyl Cellulose | 2.50 |
| Flavor | 1.00 |
| Water QS to | 100.00 |

This dentifrice exhibits anticalculus, antiplaque and antistain activity.

EXAMPLE 6

The plaque inhibiting characteristics of the AHP-containing compositions of this invention are illustrated by this Example. Ten subjects took part in a four day study during each phase of which, no other oral hygiene was employed (e.g. no tooth brushing or the like). The subjects were given a complete dental prophylaxis and entered each treatment phase of the study. Each subject rinsed for one minute, twice daily, with approximately 15 ml. or each treatment solution listed in Table 6. At the end of each treatment phase, plaque on all surfaces were scored according to the method of Silness and Loe (1964) Periodontal disease in Pregnancy, Acta. Odontol. Scand. 22:121–135. The placebo rinse treatment consisted of the solution of Sample 2 of Example 1 with the exception that it contained no CHX or AHP. The 0.12% CHX rinse treatment consisted of the solution of Sample 2 of Example 1.

TABLE 6

| Treatment | Mean Plaque Score | % Plaque Reduction |
|---|---|---|
| Placebo Rinse | 1.60 | 0 |
| CHX Rinse | 0.57 | 64 |
| CHX & AHP Rinse | 0.43 | 73 |

As can be seen the CHX rinse as well as the stain reducing CHX and AHP rinse of this invention results in significant plaque reduction.

EXAMPLE 7

Solutions were prepared containing 25 ppm of triclosan in ethanol; 25 ppm of Gantrez S-97 in water; and each of 1,2,3 and ppm of AHP in water.

When each of the AHP solutions is mixed with the triclosan solution and the triclosan and gantrez S-97 solutions, it is observed that crystal growth of hydroxyapatite is slower than occurs with water alone, thereby indicating effectiveness of mixtures of AHP and triclosan and/or AHP, triclosan and Gantrez in retarding hydroxyapatite formation.

EXAMPLE 8

Mouthrinses having antiplaque and anticalculus activity having the following formulations were prepared:

| | Parts | | | |
|---|---|---|---|---|
| | A | B | C | D |
| Sorbitol | 30.00 | 30.00 | 30.00 | 30.00 |
| Glycol | 9.50 | 9.50 | 9.50 | 9.50 |
| Gantrez S-97 | — | — | 2.00 | 2.00 |
| Sodium Lauryl Sulfate | 2.50 | 2.50 | 2.50 | 2.50 |
| AHP | 0.50 | 1.00 | 0.50 | 1.00 |
| Triclosan | 0.30 | 0.30 | 0.30 | 0.30 |
| Flavor Oil | 0.95 | 0.95 | 0.95 | 0.95 |
| Water | Q.S. to 100 | Q.S. to 100 | Q.S. to 100 | Q.S. to 100 |

EXAMPLE 9

Toothpaste

| Component | Weight Percent |
|---|---|
| Azacycloheptane-2, 2-diphosphonic acid (AHP) | 1.0 |
| Sorbitol solution, 70% active, aqueous (22.5 wt %) | 32.1 |
| Glycerol | 11.0 |
| Carrageenan gum | 0.5 |
| Sodium Fluoride | 0.24 |
| Gantrez S-97, pharmaceutical grade (SAPP)[1] | 0.5 |
| Sodium Lauryl Sulphate | 1.2 |
| Zeodent (Registered Trade Mark) 113[2] | 17.0 |
| Syloid (Registered Trade Mark) 244[3] | 3.0 |
| Fumed Silica, Thickening Agent | 0.3 |
| Triclosan | 0.3 |
| Saccharin | 0.06 |
| Flavour (containing terpenes and mints) | 1.0 |
| Water, Deionized | 31.8 |
| | 100.00 |

[1]Linear copolymer of maleic anhydride and vinyl methyl ether, of molecular weight of about 1,090,000 (by gel permeation chromatography vs. polyethylene glycol), manufactured by GAF Corp.
[2]Silica dental polishing agent, manufactured by J.M. Huber Corp.
[3]Silica thickening agent.

A toothpaste of the above formula is made in the manner described earlier in this specification, essentially following normal toothpaste manufacturing procedures.

The described toothpaste formula possesses anticalculus and significant antiplaque properties and also acts to harden teeth, due to its content of a fluoride source (sodium fluoride), and is an effective tooth cleaner and polisher, due to its contents of surfactant and silica polishing agent. When the fluoride is omitted from the formula its tooth hardening action is lost but the anticalculus effect of the combination of AHP and SAPP is still obtained.

In the given formula, the Zeodent 113 may be replaced by other Zeodent type polishing agents and/or by other polishing agents such as dicalcium phosphate, calcium carbonate, insoluble sodium metaphosphate and tricalcium phosphate, but the finely divided silica polishing agents are preferred and are less likely to interfere to any extent with the anticalculus action of the AHP. The sodium lauryl sulphate detergent may be replaced by other orally acceptable detergents, such as other alkali metal alkyl sulphates of 8 to 20 carbon atoms, preferably of 10 to 18 and more preferably of 12 to 16 carbon atoms in the alkyls thereof. Alternatively, other anionic, nonionic and amphoteric detergents may be employed in place of the sodium lauryl sulphate, e.g. sodium cocomonoglyceride sulphate, sodium linear tridecylbenzene sulphonate, potassium N-lauroyl sarcosine, N-lauroyl, N-methyl, taurate, the myristic acid ester of 1, 2-dihydroxypropane sulphonate, the condensation product of a $C_{12-15}$ linear alcohol and 7 moles of ethylene oxide, the condensation product of a $C_{14-15}$ linear alcohol and about 11 moles of ethylene oxide, Pluronic F-68, Pluronic L-44, lauryl ammonium sulphonic acid betaine and Standapol (Registered Trade Mark) AB-45, either separately of in mixtures. The thickener system may be replaced by other thickeners, such as carob bean gum, hydroxymethyl cellulose, Laponites (Registered Trademark) and alginates. In place of part of the glycerol/sorbitol humectant system there may be substituted propylene glycol, polypropylene glycol and/or mannitol, and the fluoride employed may be sodium monofluorophosphate, stannous fluoride, sodium fluorosilicate or calcium fluoride. Instead of saccharin, as the artificial sweetener, aspartame may be used and the flavour may be based principally or partially on limonene and may contain menthol or other physiologically cooling agent to give it a special appeal.

It will normally be desirable for the polishing agent and any other insoluble materials present in the formula to be of particle sizes no greater than 5 microns in effective diameter and preferably they will be no larger than of a mean particle size of 2 microns, so as to avoid any scratching of tooth enamel during brushing of the teeth. When the composition is not to be applied with pressure against the teeth larger sized component particles may be tolerated. However, for another variation of the invented compositions, tablets, which may include known tabletting compounds, such as clays and magnesium stearate, it will normally be desirable to limit the insoluble components to the sizes previously given.

When gel dentifrices are to be produced, the formula of this example will be varied accordingly to produce the desired gel form, which may desirably be transparent or translucent, due to employment of a polishing agent of the Syloid or similar type, which is of about the same refractive index as that of the gelling agent/water medium. Such polishing agents are colloidal silicas.

The various modified formulas of Example 9 and the following Examples described herein are also effective anticalculus and antiplaque toothpastes, gel dentifrices, etc., when the same AHP and SAPP are employed, and are also effective when other AAP's and SAP's, sulphonates, phosphinates, phosphonates or carboxylates within the description of this specification are substituted and when noncationic antimicrobial agents described herein replace triclosan. Similarly, such compositions and the composition of the formula given are useful in inhibiting development of calculus and plaque in humans who brush their teeth with such a composition. For best results, such toothbrushings should be twice a day for at least one minute each, preferably two minutes, and brushing should continue for a least a month, preferably longer, and more preferably always. Other adjuvants may be included in the various formulas described, such as water soluble alkali metal polyphosphates, e.g. sodium pyrophosphate, to give the compositions additional desirable properties, such as tartar inhibiting action, etc. Unlike sodium pyrophosphate, which can be adversely affected by mouth enzymes, and may be protected by fluoride and SAPP against enzymatic inactivation, the AAP is stable in the presence of such enzymes and requires no stabilizer. However, if pryophosphate is present in the formula to promote antitartar action the SAPP present with the AAP will perform the dual functions of increasing anticalculus action and stabilizing the pyrophosphate against enzymatic action (and the fluoride source will also exert such a stabilizing effect, if present).

EXAMPLE 10

Mouthrinse

| Component | Weight Percent |
|---|---|
| Azacycloheptane-2, 2-diphosphonic acid (AHP) | 0.5 |
| Gantrez S-97, pharmaceutical grade (SAPP) | 0.25 |
| Glycerol | 1.0 |
| Sodium Fluoride | 0.05 |
| Nonionic Detergent[4] | 1.0 |
| Triclosan | 0.03 |
| Flavour | 1.0 |
| Sodium Saccharin | 0.03 |
| Water | 96.14 |
| | 100.00 |

[4]Pluronic F-108 or F-127, manufactured by BASF Wyandotte, Inc.

A mouthrinse of the above formula is made by mixing together the various components thereof to make a finished product suitable for use in freshening the breath and in making the teeth less liable to develop plaque and calculus deposits thereon after such repeated uses, preferably for a month or more, with application twice daily.

In variations of the formula when Luviform FA 139 (BASF) is substituted for the Gantrez S-97, an effective antiplaque and anticalculus product is obtained. Also, there is desirably substituted for 15% of the water an equal weight of ethanol (95%), which helps to solubilize the components better and has a desirable solvent action on organic materials in the saliva and on the teeth. Additionally, to aid in cleaning the oral cavity an the tooth surfaces there may desirably be present in the mouthrinse about 0.2–0.5% of surfactant (sodium lauryl sulphate is preferred).

EXAMPLE 11

Chewing Gum

| Component | Weight Percent |
|---|---|
| Azacycloheptane-2, 2-diphosphonic acid (AHP) | 0.2 |
| Gantrez S-97, pharmaceutical grade (SAPP) | 0.25 |
| Sorbitol/mannitol mixture (50:50) | 35.0 |
| Triclosan | 0.3 |
| Flavour, including 0.03% saccharin | 2.0 |
| Chicle Base | 20.0 |
| Binder (starch) | 10.0 |
| Filler (talc) | 32.25 |
| | 100.00 |

Such a chewing gum is effective in inhibiting plaque and calculus deposition on teeth if chewed daily, preferably several times daily. It is also effective when the proportion of the AHP to SAPP is changed ±10, 20 and 30%, while still remaining within the ranges previously given in this specification. For best antiplaque and anticalculus effects, the gum should be chewed one or more times daily for one or more minutes at a time for at least a month.

EXAMPLE 12

Lozenge

| Component | Weight Percent |
| --- | --- |
| Azacycloheptane-2, 2-diphosphonic acid (AHP) | 0.20 |
| Gantrez AN 119 (SAPP) | 0.25 |
| Sorbitol | 97.70 |
| Triclosan | 0.30 |
| Sodium Saccharin | 0.15 |
| Magnesium Stearate (tabletting agent) | 0.40 |
| Emulsifier (Polysorbate 20) | 1.00 |
| | 100.00 |

A lozenge of the above formula is made by melting the sorbitol and dissolving/dispersing the other components in it, after which the mix is allowed to solidify at room temperature. The lozenges so made are effective in combatting plaque and calculus formation on teeth when used at lease once a day for a month but preferably they are used twice daily for two or more months or longer and the antiplaque and anticalculus results are even better.

Instead of employing sorbitol as the base, other such sugars and sugar alcohols may be substituted, e.g. mannitol, sucrose and glucose, or mixtures thereof, and similar results will be obtained. Alternatively, gums and gelatins may be the bases for the lozenges or candies, and the proportions of the active component may be increased, to as much as 1% of each of the AAP and the SAPP. Triclosan may range from 0.1 to 0.6%.

EXAMPLE 13

Tooth Powder

| Component | Weight Percent |
| --- | --- |
| Azacycloheptane-2, 2-diphosphonic acid (AHP) | 1.0 |
| Gantrez S-97, pharmaceutical grade (SAPP) | 1.0 |
| Sodium Lauryl Sulphate | 0.5 |
| Triclosan | 0.3 |
| Zeodent 113 | 97.2 |
| | 100.00 |

The tooth powder of the above formula is made by mixing together the formula components in a suitable powder mixer. In a preferred formula there is also present about 0.2–0.8% of a suitable flavour, preferably of the mint type, e.g. peppermint, spearmint, and triclosan may range from 0.1 to 0.6%.

The tooth powder made is good for cleaning the teeth and for protecting them against development of plaque and calculus, with resulting gum irritation that such can cause. With triclosan present, the powder also protects against bacterial growth that can cause the appearance of unsightly and harmful plaque. Use of the tooth powder should be regular, at least twice daily for at least a month and preferably for longer.

EXAMPLE 14

The following toothpaste is prepared for effectively inhibiting plaque and calculus formation:

| Component | Weight Percent |
| --- | --- |
| Azacycloheptane-2, 2-diphosphonic acid (AHP) | 1.0 |
| Sorbitol solution, 70% active, aqueous | 32.1 |
| Glycerol | 11.0 |
| Carrageenan Gum | 0.5 |
| Sodium Fluoride | 0.24 |
| Polyvinyl phosphonic acid (PVPA, mol. wt % of about 10,000) | 0.5 |
| Sodium Lauryl Sulphate | 1.2 |
| Zeodent 113[2] | 17.0 |
| Syloid 244[3] | 3.0 |
| Triclosan | 0.3 |
| Fumed Silica, thickening agent | 0.3 |
| Saccharin | 0.06 |
| Flavour (containing terpenes and mints) | 1.0 |
| Water, deionized | 31.8 |
| | 100.00 |

[2]Silica dental polishing agent, manufactured by J. M. Huber Corp.
[3]Silica thickening agent.

EXAMPLE 15

The following mouthrinse is prepared for effectively inhibiting plaque and calculus formation:

| Component | Weight Percent |
| --- | --- |
| Azacycloheptane-2, 2-diphosphonic acid (AHP) | 0.5 |
| PVPA (mol. wt. = 10,000) | 0.25 |
| Glycerol | 1.0 |
| Sodium Fluoride | 0.05 |
| Nonionic Detergent[4] | 1.0 |
| Triclosan | 0.3 |
| Flavour | 1.0 |
| Sodium Saccharin | 0.03 |
| Water | 95.87 |
| | 100.00 |

[4]Pluronic F-108 or F-127, manufactured by BASF Wyandotte, Inc.

The described products, the formulas of which have been given above, may be modified by replacement of active and supplementary components with others that were previously named and referred to herein and the proportions thereof may be changed, so long as they remain within the ranges recited herein, and effective anticalculus compositions will result. While the various products, being of substantially different types, may have different properties (and may be of different physical states) normally they will be of pH's in the range of 6 to 11, preferably 7 to 9 or 10, e.g. about 7 or 8 at a 1% solution or dispersion in water at 25° C. Various other compositions for application to the teeth may be made in similar ways, such as tooth hardening agents, gel dentifrices with the tooth hardeners including a source of fluoride, such as 0.5% of sodium fluoride. Also, in all the working examples when the AHP is replaced by azacyclohexane-2, 2-diphosphonic acid or by an AAP of the formula given wherein n is 3 and R is ethyl, or by a sodium salt thereof and when the SAPP is any of the Gantrezes described herein or is a suitable SAP improved anticalculus activity is obtainable.

The invention has been described herein with references to working examples and specific embodiments thereof but is not to be limited to these because one of skill in the art with the present specification before her or him will be able to utilize substitutes and equivalents without departing from the invention.

What is claimed is:

1. An oral care composition comprising
   (a) an effective amount of a source of an azacycloalkane-2,2-diphosphonate anion as an anticalculus agent;
   (b) an effective amount of 5-chloro-2-(2,4-dichlorophenoxy) phenol; and
   (c) a toxicologically acceptable oral carrier.

2. A composition according to claim 1 wherein the anticalculus agent is a salt of 1-azacycloheptylidene-2,2-diphosphonic acid.

3. A composition according to claim 1 which additionally comprises a source of an effective amount of fluoride ion.

4. A composition according to claim 2 which additionally comprises a source of an effective amount of fluoride ion.

5. A method of preventing the accumulation of calculus and plaque on dental enamel comprising contacting said dental enamel with a composition according to claim 1.

6. A method of preventing the accumulation of calculus and plaque on dental enamel comprising contacting said dental enamel with a composition according to claim 2.

7. A method of preventing the accumulation of calculus and plaque on dental enamel comprising contacting said dental enamel with a composition according to claim 3.

8. A method of preventing the accumulation of calculus and plaque on dental enamel comprising contacting said dental enamel with a composition according to claim 4.

9. An oral care composition according to claim 1 wherein said composition additionally contains a synthetic anionic polymeric polycarboxylate of a molecular weight in the range of about 5,000 to 2,000,000 in an amount effective to increase anticalculus action of the azacycloalkane phosphonate anion.

* * * * *